(12) United States Patent
Slepian

(10) Patent No.: US 11,179,065 B2
(45) Date of Patent: Nov. 23, 2021

(54) SYSTEMS, DEVICES, AND METHODS FOR DETERMINING AN OVERALL MOTION AND FLEXIBILITY ENVELOPE

(71) Applicant: Arizona Board of Regents on Behalf of the University of Arizona, Tucson, AZ (US)

(72) Inventor: Marvin J. Slepian, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 312 days.

(21) Appl. No.: 16/309,784

(22) PCT Filed: Jun. 16, 2017

(86) PCT No.: PCT/US2017/037933
§ 371 (c)(1),
(2) Date: Dec. 13, 2018

(87) PCT Pub. No.: WO2017/218930
PCT Pub. Date: Dec. 21, 2017

(65) Prior Publication Data
US 2019/0125220 A1    May 2, 2019

Related U.S. Application Data

(60) Provisional application No. 62/351,260, filed on Jun. 16, 2016.

(51) Int. Cl.
*A61B 5/00* (2006.01)
*A61B 5/0205* (2006.01)
(Continued)

(52) U.S. Cl.
CPC .......... *A61B 5/1121* (2013.01); *A61B 5/0022* (2013.01); *A61B 5/0077* (2013.01);
(Continued)

(58) Field of Classification Search
CPC ... A61B 5/1121; A61B 5/6847; A61B 5/1124; A61B 5/0205; A61B 5/4884
See application file for complete search history.

(56) References Cited

U.S. PATENT DOCUMENTS

2008/0262812 A1    10/2008  Arata et al.
2012/0022616 A1     1/2012  Garnham et al.
(Continued)

FOREIGN PATENT DOCUMENTS

WO   WO-2015139145 A1 *  9/2015  ........... A61B 5/0075

OTHER PUBLICATIONS

Joris M. Lambrecht, Miniature Low-Power Inertial Sensors: Promising Technology for Implantable Motion Capture Systems, Nov. 2014, IEEE Transactions on Neural Systems and Rehabilitation Engineering, vol. 22, No. 6 (Year: 2014).*
(Continued)

*Primary Examiner* — Eric F Winakur
*Assistant Examiner* — Jasim Ahmad Naeem
(74) *Attorney, Agent, or Firm* — Lathrop GPM LLP; Curtis A. Vock

(57) ABSTRACT

Systems, methods and software products determine an overall motion and/or flexibility envelope for an individual. Movement and position data of the individual is captured and processed to generate an overall motion and/or flexibility envelope for the individual defining overall motion and/or flexibility of the individual. The systems include a flexibility server with memory and a processor adapted to receive movement and position data of the individual, a motion and/or flexibility analyzer, implemented as machine readable instructions stored in the memory and executed by the digital processor, capable of processing the movement and position data to generate an overall motion and/or
(Continued)

flexibility envelope for the individual defining overall motion and/or flexibility of the individual.

18 Claims, 10 Drawing Sheets

(51) Int. Cl.
    *A61B 5/11*           (2006.01)
    *G06T 7/292*        (2017.01)
    *A61B 5/021*       (2006.01)
    *A61B 5/024*       (2006.01)

(52) U.S. Cl.
    CPC .......... *A61B 5/0205* (2013.01); *A61B 5/1124* (2013.01); *A61B 5/1126* (2013.01); *A61B 5/1128* (2013.01); *A61B 5/4266* (2013.01); *A61B 5/4884* (2013.01); *A61B 5/6847* (2013.01); *G06T 7/292* (2017.01); *A61B 5/021* (2013.01); *A61B 5/02055* (2013.01); *A61B 5/02405* (2013.01); *A61B 5/11* (2013.01); *A61B 2562/0204* (2013.01); *A61B 2562/0219* (2013.01); *A61B 2562/0223* (2013.01); *A61B 2562/0247* (2013.01); *A61B 2562/0257* (2013.01); *A61B 2562/0261* (2013.01)

(56) References Cited

U.S. PATENT DOCUMENTS

| | | |
|---|---|---|
| 2012/0116548 A1 | 5/2012 | Goree et al. |
| 2013/0123667 A1 | 3/2013 | Komatireddy et al. |
| 2013/0339908 A1 | 12/2013 | Bailey et al. |
| 2015/0133820 A1* | 5/2015 | Zohar .................. A61B 5/1121 600/595 |
| 2015/0318015 A1 | 11/2015 | Bose et al. |
| 2015/0332004 A1 | 11/2015 | Najafi et al. |
| 2015/0375106 A1 | 12/2015 | Liu |
| 2016/0150966 A1 | 6/2016 | Koninklijke |

OTHER PUBLICATIONS

International Search Report of PCT/US2017/037933 dated Oct. 23, 2017, 3 pp.
Written Opinion of PCT/US2017/037933 dated Oct. 23, 2017, 8 pp.
International Report on Patentability of PCT/US2017/037933 dated Dec. 18, 2018, 9 pp.

* cited by examiner

SYSTEMS, DEVICES, AND METHODS FOR DETERMINING AN OVERALL MOTION AND FLEXIBILITY ENVELOPE

RELATED APPLICATIONS

This application claims priority to U.S. Patent Application Ser. No. 62/351,260, titled "Systems, Devices, and Methods for Determining an Overall Motion and Flexibility Envelope", filed Jun. 16, 2016, and incorporated herein by reference.

BACKGROUND

Movement is a critical activity and state for all organisms, including man. Movement may be considered as being of two types: complete translation or translocation of an organism from one location to another—examples here being walking, running, somersaulting, falling or the like; or alternatively movement may be considered the displacement, bending, angulation, rotation, or other positional alteration of the organism or components of the organism—e.g. a limb, the head and neck, the upper torso, the trunk without significant translocation of the overall organism as in going from location A to location B. Although movement and flexibility of particular joints may be quantified, there is no measurement or quantification of overall movement and flexibility of an organism.

SUMMARY

The embodiments disclosed herein are focused on translocation of an organism from one location to another. As such considering this type of movement, an organism, such as a human or animal has the ability to move all or a portion of its body, soma or corpus. Movement of the body, body part or appendage may be either active—e.g. as in bending over, lifting an arm, tilting the head and the like, actuated via internal neural commands and intention, or passive. For passive movement another individual, device or system moves the appendage such as in someone moving a test subjects arm to determine what has been colloquially referred to as range of motion, but is more accurately a "range of flexibility." Within both of these forms or movement there is a defined maximum range of movement that is three-dimensional. If one were to trace the outer perimeter and capture and visualize the entire "volume" of space covered by this movement this would be define, both quantitatively and qualitatively, the "motion or movement envelope"—i.e. for active, volitional or stimulated movement or the "flexibility envelope" for either active or passive movement of the body region, appendage, limb, head and neck, and the like being tested.

For the embodiments disclosed herein, "motion envelope" and "movement envelope" may be utilized interchangeably.

As to the "flexibility envelope," this is a region that may be equal to, larger or smaller than the motion or movement envelope. The size, volume or extent of the flexibility envelope is governed by the limberness, elasticity, laxity and otherwise overall flexible nature of the body region, appendage or limb being tested. The degree of flexibility of a given organism or test subject varies depending upon how much activity the organism regularly performs, the degree of intactness, i.e. freedom from injury, and on the age or state of health of the organism. The extent of the flexibility envelope is also governed by whether the activity performed to define the envelope is active and volitional or passive by a third party or system.

It should be understood that the motion and flexibility envelope may overlap in full or in part. For example, an individual may only be able to move a limb actively to a defined limit or cover a defined volume of space. However, with an assistant moving the limb, the range of motion may be greater, largely governed by the "flexibility" of the limb. In this case the passive "flexibility envelope" may be slightly greater than the active "motion envelope." In contrast, an individual may be able to actively move a limb to a defined degree and as such the "flexibility" and "mobility" envelopes will overlap. It is envisioned that with the embodiments disclosed herein, both the motion and/or flexibility envelopes may be defined and their degree of overlap or non-overlap determined.

For humans, motion and flexibility are typically measured individually as a single parameter for a single appendage. For example, when a person has an injury that affects an elbow joint, such as a broken arm that requires immobilization of the elbow joint to allow the bone to heal, this immobilization typically results in reduced flexibility of the elbow joint. Rehabilitation of the joint typically requires physiotherapy to improve range of motion and flexibility of the elbow joint, where motion and/or flexibility is measured in angular degrees of movement of the forearm relative to the upper arm. Despite this characterization of the movement, much information such as the full geometric excursion of the contiguous or involved tissue, appendage or limb, is not provided by this technique.

The embodiments disclosed herein, defining, quantitating, analyzing and otherwise utilizing the motion and flexibility envelope, addresses this limitation and provides novel means of completely capturing movement and flexibility information, both quantitatively and qualitatively, analyzing, storing, displaying, comparing, telemetering and otherwise utilizing this data.

In one embodiment, a method determines an overall motion and/or flexibility envelope for an individual. Movement and position data of the individual is captured and processed to generate an overall motion and/or flexibility envelope for the individual defining overall motion and/or flexibility of the individual.

In another embodiment, a system determines an overall motion and/or flexibility envelope for an individual. The system includes a flexibility server having memory and a processor and adapted to receive movement and position data of the individual, a motion and/or flexibility analyzer, implemented as machine readable instructions stored in the memory and executed by the digital processor, capable of processing the movement and position data to generate an overall motion and/or flexibility envelope for the individual defining overall motion and/or flexibility of the individual.

In another embodiment, a system determines an overall motion envelope for an individual. The system includes means for capturing motion of the individual, means for recording and analyzing said motion data, means for storing raw and processed information, means for converting the motion data into a flexibility envelope, means for displaying the flexibility envelope, and means for comparing the flexibility envelope at differing time points and under differing conditions.

In another embodiment, a method determines an overall motion and/or flexibility envelope for an individual. Movement and position data from at least one sensor or motion detection means configured with the individual is captured and analyzed to generate the overall motion and/or flexibility envelope for the individual. A display from the overall motion and/or flexibility envelope is generated to show motion and/or flexibility of the individual.

In another embodiment, a software product has instructions, stored on non-transitory computer-readable media, wherein the instructions, when executed by a computer, perform steps for determining an overall motion and/or flexibility envelope for an individual. The software product includes instructions for capturing movement data, instructions for analyzing movement data, instructions for converting data into a graphical representation of movement in either 1, 2, 3 or 4D, and instructions for comparing movement of any aspect of full or partial flexibility envelope to either another point of time of the envelope of the same individual or of a database of performance.

In another embodiment, a device portrays, compares and displays the overall motion and/or flexibility envelope.

In another embodiment, a system allows data to be sent to the cloud, be security encrypted, and then to be downloaded by appropriate, security cleared user.

In another embodiment, a series of instructions, exercises, directives to attempt to regain the motion/flexibility envelope if a decline has occurred, using any of the systems described above to monitor progress and guide therapy.

DETAILED DESCRIPTION OF THE EMBODIMENTS

Figure 1:
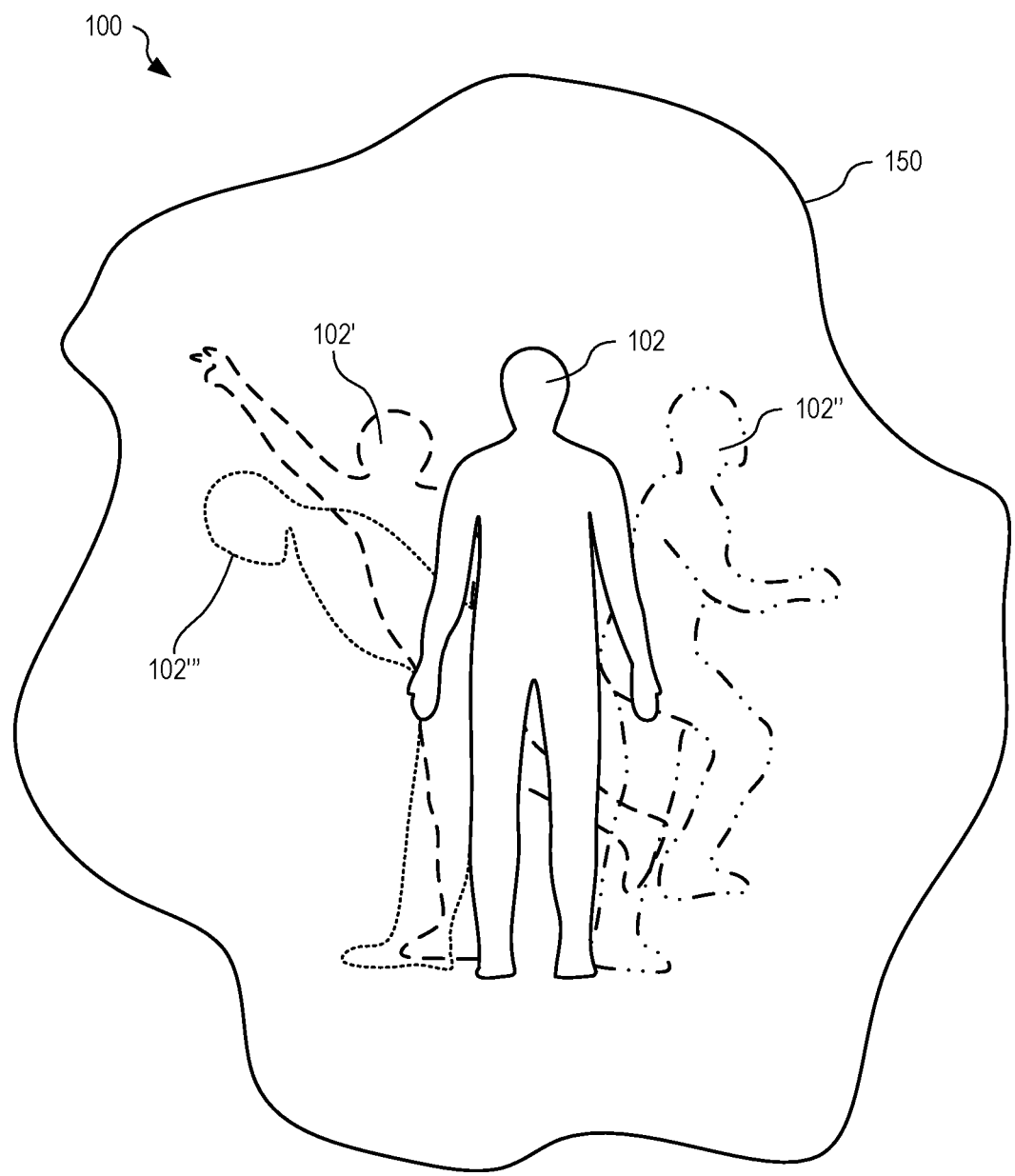
FIG. 1 is a 2-D high level visualization of one example overall motion and/or flexibility envelope for an individual human body, in an embodiment.

The embodiments disclosed herein describe systems, devices, and methods for evaluating overall movement and flexibility of an organism (e.g., the human body), of collecting quantitative information and statistics on overall movement and flexibility for different types of organisms, and for evaluating an individual organism's movement and flexibility either standalone or against changes from other interval recording of the same or against the statistical information based upon the type of organism. An organism's current overall motion and/or flexibility envelope is evaluated against a recorded overall motion and/or flexibility envelope for that individual organism or against a large database (of continuously updated—i.e. akin to machine learning) to determine trends in motion and/or flexibility over time. This overall motion and/or flexibility envelope defines motion and/or flexibility of the organism, where individual portions of the overall motion and/or flexibility envelope may be measured and defined in many various ways, such as x-y-z plane movements, pitch-roll-yaw movements, polar or circular coordinates, and so on. In addition to dimensional data (1, 2, 3 or 4)(time)D, velocity data (e.g. dx/dt), or acceleration data (dv/dt) for any point, plane or space may be characterized as well. However determined, the individual motion and/or flexibility measurements are combined to form the overall motion and/or flexibility envelope that is stored digitally and may be processed, evaluated, and presented in many recognizable and usable forms to indicate overall motion and/or flexibility of the organism or of components of the organism—e.g., a given appendage such as an arm.

In the following examples, the human body is used to illustrate the embodiments hereof, however, the systems, devices, and methods described herein may apply to any organism where overall motion and/or flexibility of movement may be measured without departing from the scope hereof.

A human body has two-hundred and thirty movable joints, each with a certain range of motion based upon the type of joint. The human body has three types of joint: (a) fibrous joints that are held together by strong connective tissue with only a slight capacity to stretch and have very little movement between the joined bones, providing great stability; (b) cartilaginous joints that allow for slight movement and occur where bone ends are covered by a somewhat flexible, compressible connective tissue called cartilage; and (c) synovial joints that consist of a capsule of connective tissue that encloses a space or cavity between the bones to allow the greatest degree of movement.

Measuring a range of motion for a specific joint on a body does not provide a complete indication of overall motion and/or flexibility of that body. Certain embodiments disclosed herein provide quantification of overall motion and/or flexibility and an overall motion and/or flexibility envelope for any organism.

In addition to distinct joints—which may be conceptualized as hinges, defined body elements—e.g. appendages (arms/legs), the head and neck and the trunk, the upper torso and the lower torso may be envisioned as "flex elements." A flex element of a corpus is herein defined as any element of the corpus of an organism—either contiguous or discontinuous (not immediately adjacent), that regardless of physical proximity are considered as a functional group. Flex elements may contain internal and external structures as well. The described embodiments provide methods, devices and systems to measure, codify, quantitate, analyze, store, telemeter and compare flex elements as well.

FIG. 1 is a 2-D high level visualization 100 of an overall motion and/or flexibility envelope 150 for an individual human body 102 (hereinafter individual 102). It should be understood that the full or max flex envelope is actually a 3-D structure at a given moment of time and a 4D structure taking time into account. The overall motion and/or flexibility envelope 150 encompasses and defines all possible non-traumatic/accidental movements of individual 102, whether active (i.e. performed by the test subject themselves or passive (i.e., performed by an exogenous testing individual, device or system). For example, as individual 102 participates in various activities (e.g., stretching individual 102', running individual 102", and bending individual 102'''), overall motion and/or flexibility envelope 150 expands to encompass the demonstrated motion and/or flexibility of individual to perform those activities.

Overall motion and/or flexibility envelope 150 changes for individual 102, for example as individual 102 ages from birth through childhood, overall motion and/or flexibility envelope 150 expands to encompass the increased motion and/or flexibility of the child as he/she becomes mobile. Where individual 102 participates in advanced training (e.g. Yoga, sporting activities, and so on), overall motion and/or flexibility envelope 150 increases as a result of the body becoming more flexible and limber through the training. As individual 102 ages through senior years towards the end of his/her life cycle, overall motion and/or flexibility envelope 150 decreases as the body loses flexibility through decline and decay. Where individual 102 changes body rhythms, such as patterns in regular activity, overall motion and/or flexibility envelope 150 also changes. For example, where individual 102 has been exercising regularly twice a week for many months, overall motion and/or flexibility envelope 150 encompasses the resulting flexibility achieved by such exercise. However, if individual 102 then stops exercising regularly, overall motion and/or flexibility envelope 150 reduces as individual 102 loses flexibility due to reduced activity. In another example, individual 102 suffers an injury and overall motion and/or flexibility envelope 150 is reduced. As individual 102 recovers from the injury, and possibly uses appropriate rehabilitation, overall motion and/or flexibility envelope 150 increases again. By comparing a current overall motion and/or flexibility envelope 150 for individual 102 with a previously recorded overall motion and/or flexibility envelope 150, changes in overall motion and/or flexibility can be determined and visualized, thereby allowing individual 102 (or a medical practitioner) to better understand the effects of rehabilitation.

Overall motion and/or flexibility envelope 150 is also affected in the short term. For example, where individual 102 has been confined to an aircraft seat as a passenger, upon disembarking from the aircraft, overall motion and/or flexibility envelope 150 of individual 102 is temporarily reduced. Similarly, after participating in a sporting activity, overall motion and/or flexibility envelope 150 of individual 102 may be temporarily extended because of warm and stretched muscles. Thus, overall motion and/or flexibility envelope 150 is continually changing.

Figure 2A:
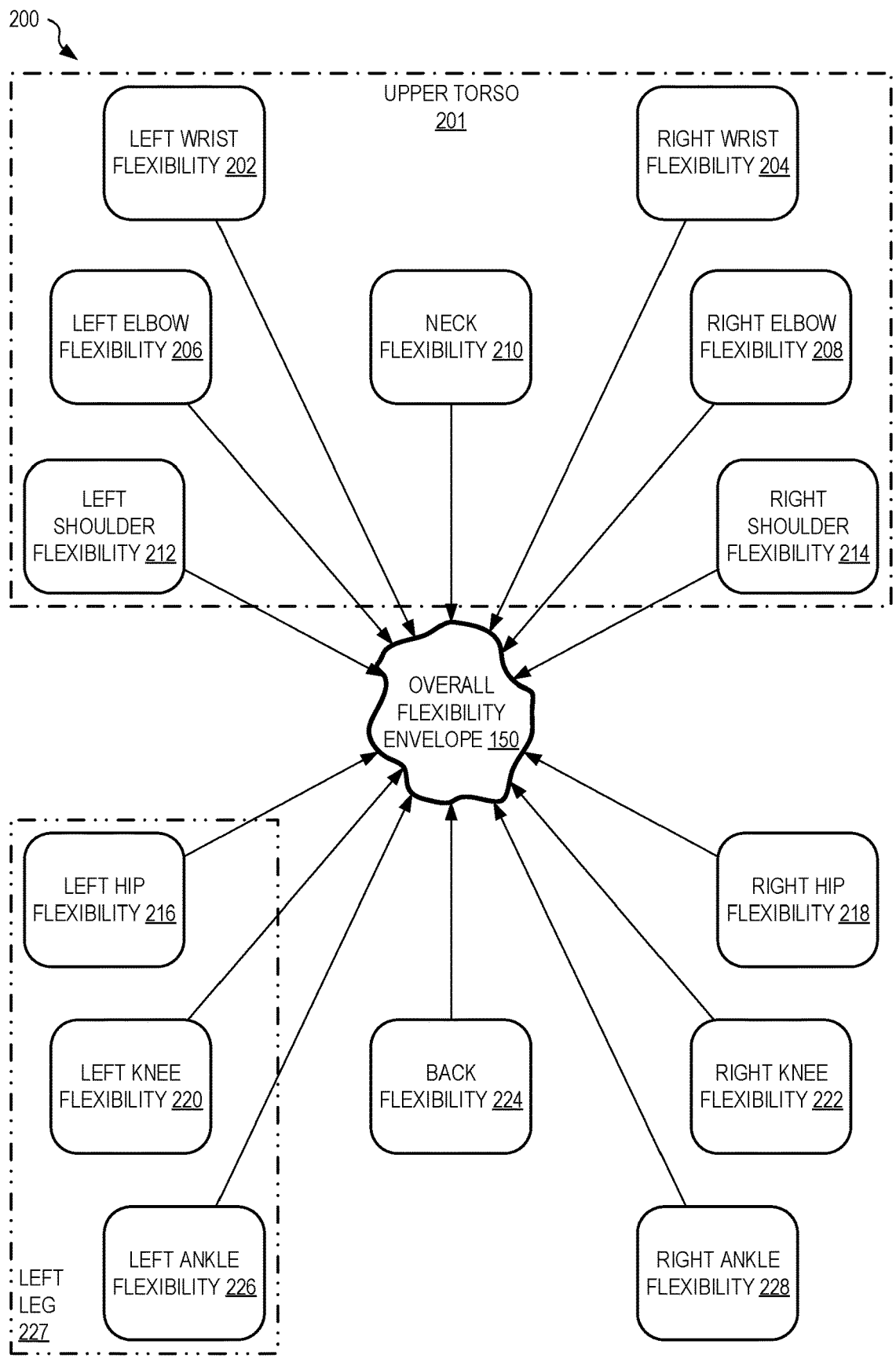
FIG. 2A shows example motion and/or flexibility components that form an overall motion and/or flexibility envelope of the individual, in an embodiment.

FIG. 2A shows example motion and/or flexibility components that form overall motion and/or flexibility envelope 150 of individual 102. Individual 102 has two-hundred and thirty movable joints. Overall motion and/or flexibility envelope 150 is based upon motion and/or flexibility of at least some of these joints. Overall motion and/or flexibility envelope 150 may be based upon motion and/or flexibility of all of these joints; however, certain ranges of motion, and this flexibility, may be difficult to measure. Therefore, in embodiments, motion and flexibility of certain joints (e.g., the fibrous joint that limits movement between the tibia and fibula bones of the lower leg) may be derived from indirect measurement.

FIG. 2A shows regional grouping of individual motion and/or flexibility components (i.e., inputs 202-214) to form an upper torso 201 flexibility element. Similarly, components 216, 220, and 226 may be regionally grouped as a left leg 227 flexibility element. Other regions may be similarly grouped, where groups may be nested and overlapped.

Figure 2B:
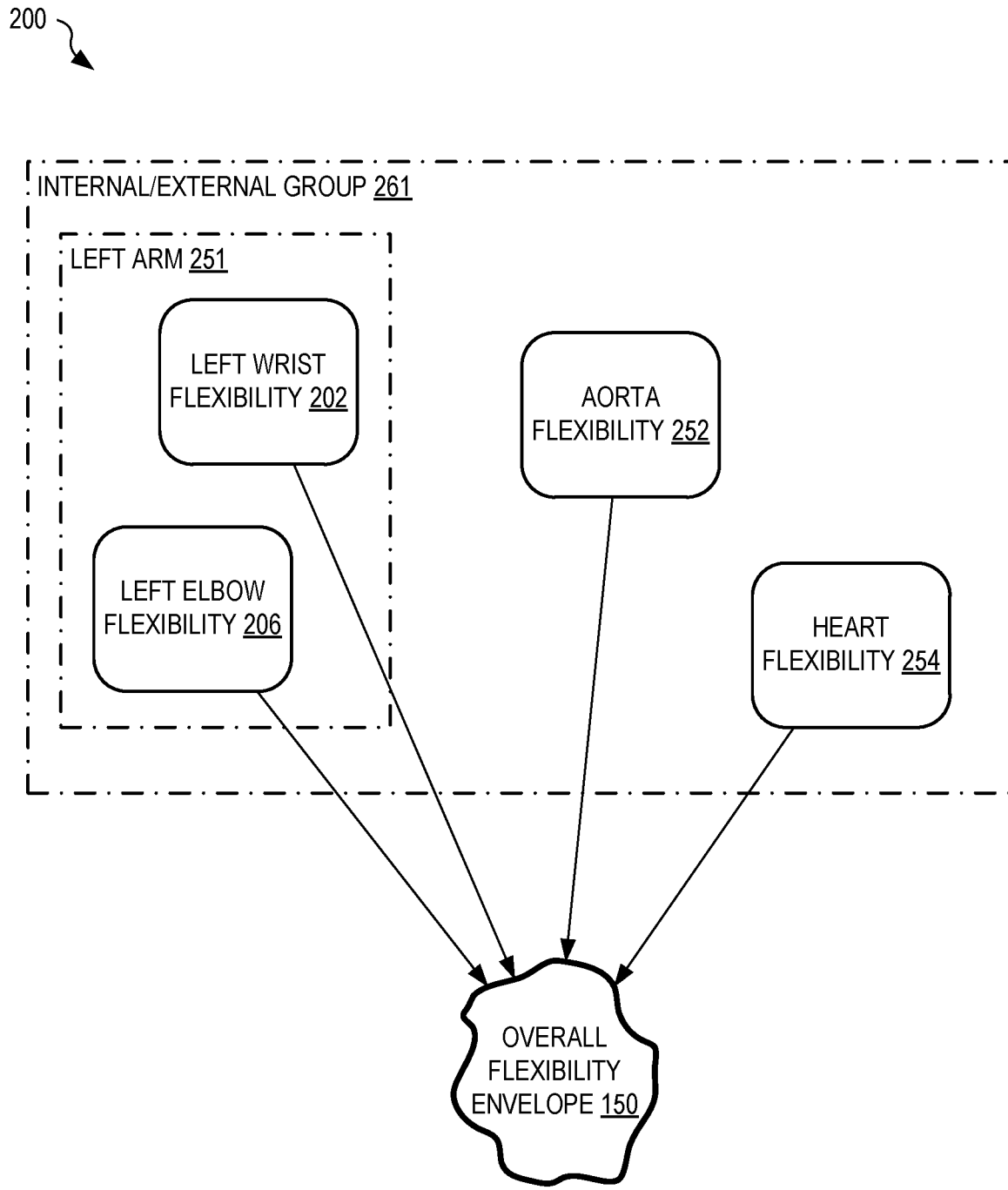
FIG. 2B shows an example grouping of external and internal components to form the internal/external group of FIG. 2A.

FIG. 2B shows example grouping of external and internal components to form an internal/external group 261. That is, external components of a left arm 251 flexibility element may be grouped with internal components such as aorta flexibility 252 and heart flexibility 254 to form internal/external group 261. In the case of internal components, such as aorta flexibility 252 and heart flexibility 254, one or more sensors may be implemented within the body of individual 102 and communicatively connected with a relay device (e.g., relay device 304 of FIG. 3) that collects and relays data wirelessly from these internal sensors.

In the example of FIGS. 2A and 2B, overall motion and/or flexibility envelope 150 is illustratively shown derived from fourteen different motion and/or flexibility inputs 200: left wrist motion and/or flexibility 202, right wrist motion and/or flexibility 204, left elbow motion and/or flexibility 206, right elbow motion and/or flexibility 208, neck motion and/or flexibility 210, left shoulder motion and/or flexibility 212, right shoulder motion and/or flexibility 214, left hip motion and/or flexibility 216, right hip motion and/or flexibility 218, left knee motion and/or flexibility 220, right knee motion and/or flexibility 222, back motion and/or flexibility 224, left ankle motion and/or flexibility 226, and right ankle motion and/or flexibility 228. Many of these motion and/or flexibility inputs 200 are complex (i.e., combining multiple planes and ranges of motion). For clarity of illustration, FIG. 2 does not show all possible motion and/or flexibility inputs 200. As noted above, the human body has two-hundred and thirty movable joints; thus, overall motion and/or flexibility envelope 150 may be derived from many other motion and/or flexibility inputs without departing from the scope hereof.

Overall motion and/or flexibility envelope 150 may be defined, in part, as motion in different planes of appendages of individual 102. Neck motion and/or flexibility 210 may be derived from multiple measurements of motion and/or flexibility. For example, individual 102 may be able to move his/her head backwards and forwards over a certain range in a first plane, sideways over a certain range in a second plane, and rotate his/her head through a certain range in a third plane. These ranges and planes combine to form neck motion and/or flexibility 210.

Given the number of joints in the human body, this overall motion and/or flexibility envelope is complex. For example, measurement of movement of a single joint is only part of the overall motion and/or flexibility envelope. Thus, in part, the overall motion and/or flexibility envelope is a measurement of all motion and/or flexibility of the body.

Capabilities and actions of individual 102 throughout the day depend upon the individual's motion capacity and flexibility. Thus, as a quantative measure, overall motion and/or flexibility envelope 150 provides a signature, or status, of well-being of individual 102 at a particular moment.

However, overall motion and/or flexibility envelope 150 is more than physical motion and/or flexibility. It may also include emotional states that are based upon, or may influence, the physical mobility and flexibility of the individual. For example, where the individual is stressed, his/her muscles may be tense, resulting in less motion and/or flexibility. Thus, overall motion and/or flexibility envelope 150 may include other health information that relates to, or influences, the motion and/or flexibility of the individual. That is, overall motion and/or flexibility envelope 150 is derived based upon physical motion of one or more body components, appendage or flexibility elements (i.e., groups of components). The detected physical motion is governed by the material properties of the constituent component structures—i.e. muscle, ligaments, tendons, presence of edema, blood flow, venous and lymphatic drainage and the like. In addition to physical elements, hormonal, neural and emotional (e.g. stress, fear) factors and states also modulate this motion and degree of flexibility.

Overall motion and/or flexibility envelope 150 is multi-dimensional and encompasses the entire body of individual 102. Thus, overall motion and/or flexibility envelope 150 extends far beyond simple joint range of motion measurements (e.g., movement of the elbow joint of one arm) that have a linear range—say 0-100, where 100 represents full range of motion. Simple measurement of motion range, also fails to take into account the three dimensional nature of many joint motions. Consider, for example, an individual has a broken arm that is set in a plaster cast. A simple evaluation of the individual's arm would indicate no range of motion or the lack of flexibility. However, that simple assessment provides no indication of how the individual is coping with that injury. Instead, by measuring a current overall motion and/or flexibility envelope 150 of individual 102 and comparing it to a previously recorded overall motion and/or flexibility envelope of individual 102, differences in motion and/or flexibility of other joints may indicate the further effect of the injury, and/or the plaster cast, on the entire body of individual 102.

Motion and/or flexibility of individual 102 may be determined by detecting movement of one or more body parts relative to one or more other body parts. For example, left elbow motion and/or flexibility may be determined by detecting movement of a left forearm relative to a left upper arm. Such movement may be determined by one of three ways: implantable sensors that measure movement from within the body, wearable sensors that attach to the body to determine movement, and off the body sensing, where body movements is determined using external apparatus, such as in a wired room that utilizes one or more of machines and cameras to detect body movement.

As outlined above, sensors may be implanted on, in or near body internal elements, organs or organ components. These sensors allow motion and flexibility determination of a defined "flex element." For example, if one were to track the left upper extremity and the heart and lungs—these could be defined as a "flex element" or group.

Figure 3:
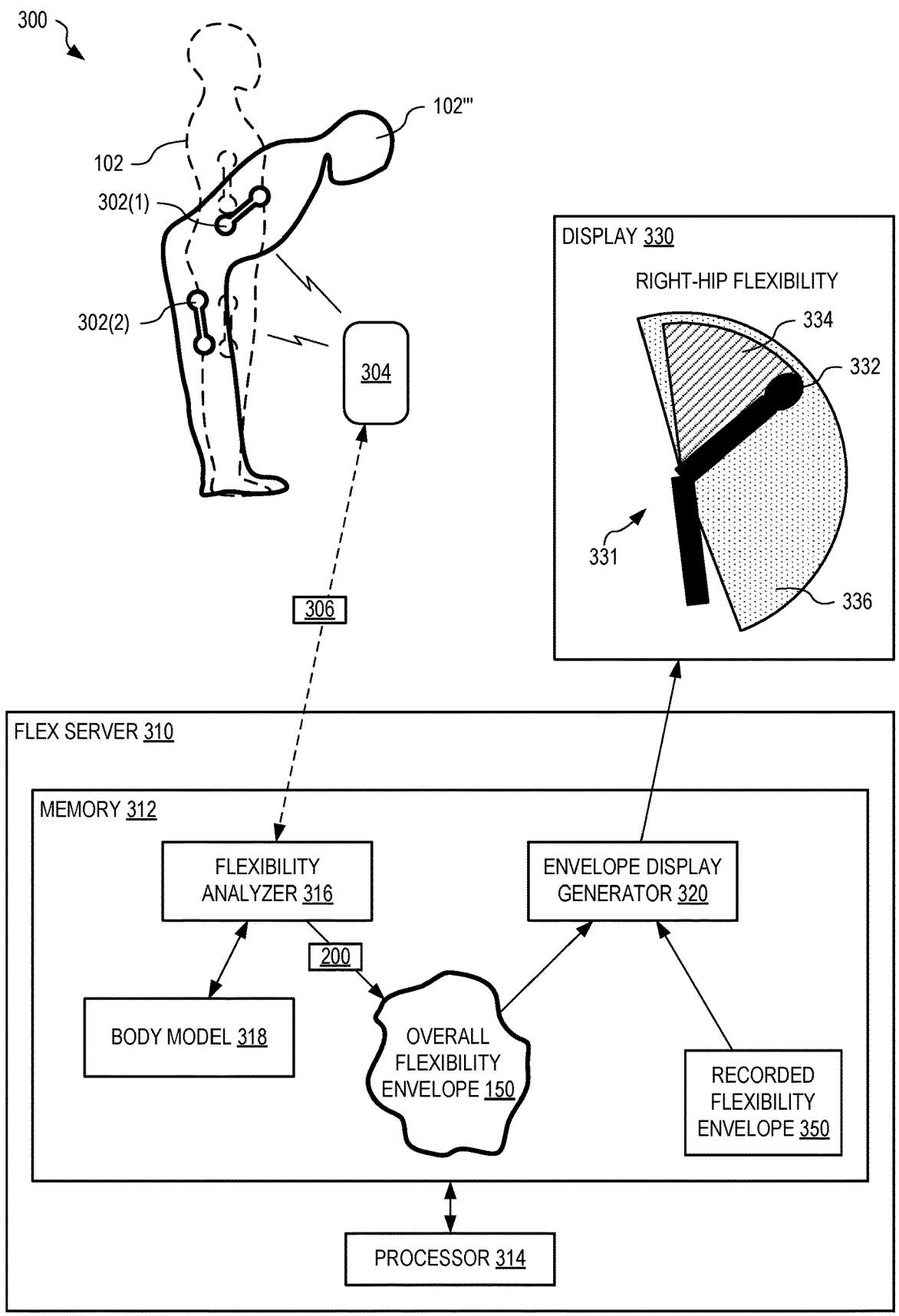
FIG. 3 shows one example system for determining the overall motion and/or flexibility envelope of FIGS. 1 and 2 for an individual, in an embodiment.

FIG. 3 shows one example system 300 for determining overall motion and/or flexibility envelope 150 for individual 102. System 300 includes a flex server 310 that has a non-transitory memory 312 and a digital processor 314. Flex server 310 is for example one or more computers enhanced to determine overall motion and/or flexibility envelope 150 of individual 102.

In one embodiment, flex server 310 is configured to receive sensor data 306 from a plurality of movement sensors 302 that are attached to, or implanted within, individual 102. Movement sensors 302 may represent one or more of strain gauges, accelerometers, gyroscopes, displacement sensors, proximity sensors, hall effect sensors, optical encoders, potentiometers, linear and rotary sensors, eddy-current sensors, reflective light sensors, pressure sensors, force sensors, tilt sensors, vibration sensors, and so on. Engineering has produced a plethora of sensors for all types of measurement and miniaturization of sensors and development of flexible circuitry allows movement sensors 302 to be implanted within the body of individual 102 or affixed on to the body of individual 102 such that continuous motion and/or flexibility measurement is possible without disruption of activity of individual 102. See for example, www.MC10inc.com (e.g. the "Biostamp"). The embodiments hereof may use any type of sensor and any format as best suited to the measurements needed.

In the example of FIG. 3, a first movement sensor 302(1) is configured at a lower-back area of individual 102, and a second movement sensor 302(2) is configured at a right-thigh area of individual 102.

Sensors 302 are wirelessly coupled to a relay device 304 that relays sensor data 306, from sensors 302 to a flexibility analyzer 316 of flex server 310. In one embodiment, relay device 304 is a smartphone that uses Bluetooth to communicate with sensors 302 and a cellular network and/or Wi-Fi for communicating with flex server 310. Relay device 304 is carried by, or positioned proximate, individual 102 and periodically receives, time stamps, and stores data from sensors 302 within an internal memory. When within range and/or communicatively connected to flex server 310, relay device 304 sends sensor data 306 to flexibility analyzer 316. In one embodiment, each sensor 302 determines its own movement in three dimensions.

Flexibility analyzer 316 has machine readable instructions stored within memory 312 that are executed by processor 314 to implement functionality for analyzing sensor data 306 and generating overall motion and/or flexibility envelope 150. Flexibility analyzer 316 manipulates a body model 318 based upon sensor data 306 to determine motion and/or flexibility inputs 200 for overall motion and/or flexibility envelope 150. Body model 318 is configured to digitally model size, weight, and movement of individual 102. In one embodiment, body model 318 is configured with the location and type of movement sensors 302 configured with individual 102. In one example of operation, flexibility analyzer 316 periodically receives sensor data 306 and uses sensor data 306 to manipulate body model 318 such that body model reflects and records movement of individual 102. In one embodiment, body model 318 stores maximum movement ranges for each joint of the human body based upon the input sensed positions of individual 102.

Flexibility analyzer 316 periodically retrieves motion and/or flexibility ranges of each joint from body model 318 and sends these ranges as motion and/or flexibility inputs 200 to overall motion and/or flexibility envelope 150. Sensors 302, flexibility analyzer 316, and body model 318 cooperate to detect movement of individual 102 and to generate flexibility inputs 200 for input to overall motion and/or flexibility envelope 150.

In one example of operation, sensor data 306 includes three dimensional position and/or movement information for each sensor 302. Flexibility analyzer 316 manipulates body model 318 based upon the received sensor data 306, such that body model 318 simulates movement of individual 102. For example, as shown in FIG. 3, as individual 102 bends at the waist, to the position shown as individual 102''', body model 318 is manipulated to follow the movement indicated within sensor data 306 for sensors 302(1) and 302(2). It is noted that other parts of body model 318 also move to achieve the defined movement. For example, the shoulders, arms, and head have also moved relative to the right thigh (sensor 302(2)), although they remain positioned relatively stationary relative to the lower back (sensor 302(1)). Thus, by correctly modelling movements sensed by sensors 302(1) and (2), movement of other body parts and joints may be derived, even when sensors are not configured to directly measure those movements.

Flexibility analyzer 316 then reads flexibility ranges (including derived flexibility) of the right hip joint, from body model 318 and inputs right-hip flexibility 218 to overall motion and/or flexibility envelope 150. Since body model 318 also determines flexibility of other joints, even when not directly measured, even without full sensor instrumentation of individual 102, body model 318 may derive movement and thus flexibility ranges of other joints.

In one embodiment, flex server 310 also includes an envelope display generator 320 that interactively generates a display 330 illustrating at least part of overall motion and/or flexibility envelope 150. In the example of FIG. 3, display 330 shows right hip flexibility resulting from the illustrated bending at the waist of individual 102.

The greater the number of sensors 302 applied to different parts of individual 102, the greater the accuracy of body model 318, and thus the greater the accuracy of overall motion and/or flexibility envelope 150.

Envelope display generator 320 may be interactive to allow a user (e.g., a doctor or individual 102) to selectively view certain types of motion and/or flexibility within display 330. Where overall motion and/or flexibility envelope 150 contains many different types of movement, the user may elect to view one or more of these movements on display 130.

In the example of FIG. 3, display 330 shows a graphical representation 331 of a 'stick' FIG. 332 that represents individual 102, and a flexibility range 334 that represents the maximum range of right-hip motion and/or flexibility achieved by individual 102. In one embodiment, memory 312 also stores a recorded motion and/or flexibility envelope 350. In one embodiment, recorded motion and/or flexibility envelope 350 represents average motion and/or flexibility a normal healthy individual of a certain body type and age. In another embodiment, recorded motion and/or flexibility envelope 350 represents a previously recorded overall motion and/or flexibility envelope 150 of individual 102. Based upon recorded motion and/or flexibility envelope 350, generator 320 may concurrently display expected motion and/or flexibility and/or previously achieved motion and/or flexibility of individual 102 as motion and/or flexibility range 336. Thus, the user may compare current motion and/or flexibility of individual 102 to expected or previously recorded motion and/or flexibility envelope 350. For example, an expected overall motion and/or flexibility envelope may be based upon an average of similar individuals, or based upon one or more of a current age, physical condition, injury status, of the individual. For clarity of illustration, the example of FIG. 3 shows a two dimensional motion and/or flexibility range; however, system 300 may display multiple motion and/or flexibility ranges from overall motion and/or flexibility envelope 150 concurrently without departing from the scope hereof. Further, based upon overall motion and/or flexibility envelope 150, system 300 may display motion and/or flexibility ranges corresponding to any joint of individual 102, even when that motion and/or flexibility is not directly measured.

Figure 4:
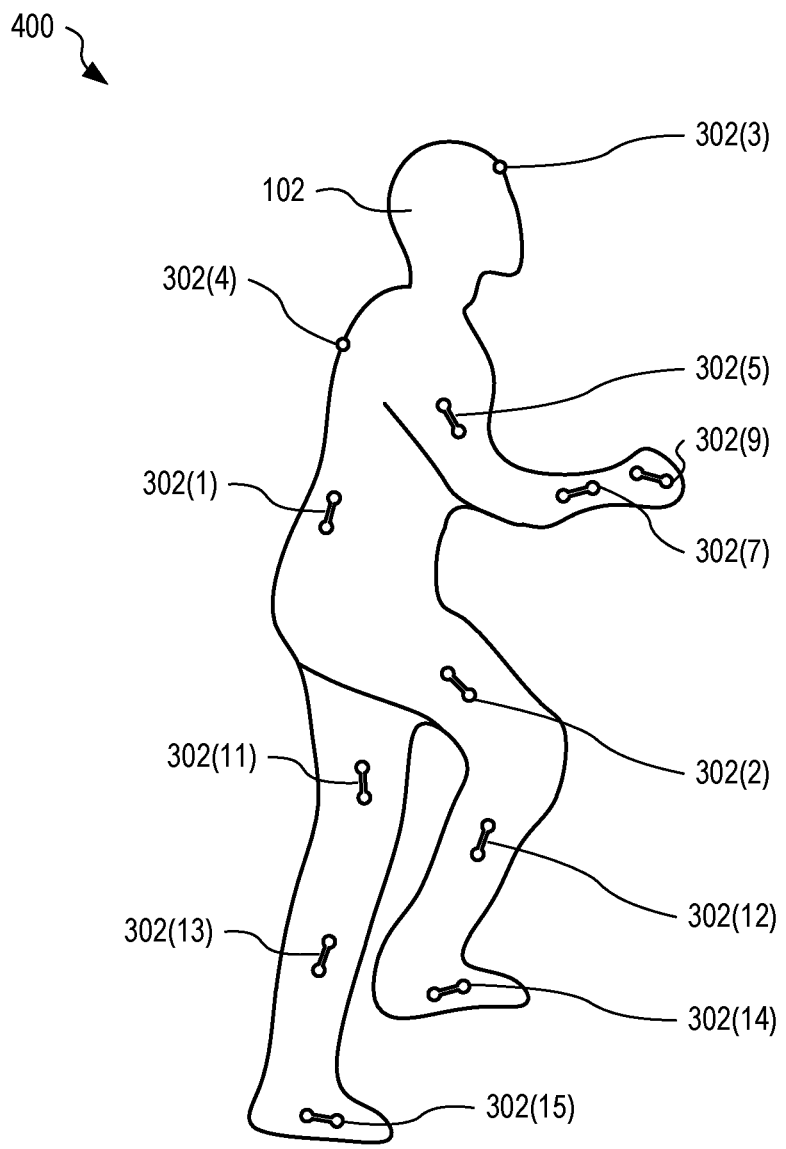
FIGS. 4 and 5 show a right side view and a front view of the individual of FIG. 3 illustrating example positioning of sensors, in an embodiment.
Figure 5:
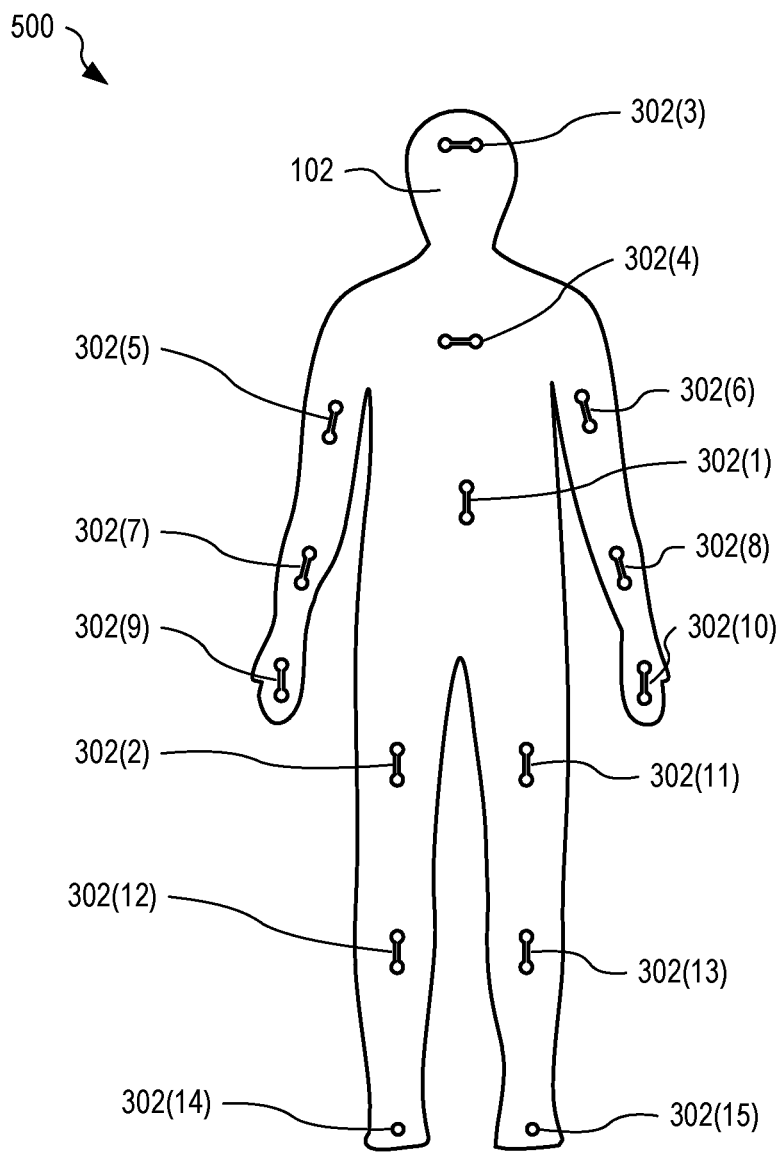

FIG. 4 is a right side view 400 of individual 102 and FIG. 5 is a front view 500 of individual 102, each view 400, 500 illustrating example positioning of sensors 302 on individual 102. FIGS. 4 and 5 are best viewed together with the following description.

Continuing with the example of FIG. 3, sensor 302(1) is positioned at the lower-back area of individual 102 and sensor 302(2) is positioned at a right-thigh area of individual 102. Sensor 302(3) is positioned on the head of individual 102 and measures head movement. In one embodiment, sensor 302(3) is configured with a hat worn by individual 102. Sensor 302(4) is positioned at the upper back (between scapula) of individual 102. Sensor 302(5) is positioned on an upper right arm of individual 102. Sensor 302(6) is positioned on an upper left arm of individual 102. Sensor 302(7) is positioned on a right forearm of individual 102. Sensor 302(8) is positioned on a left forearm of individual 102. Sensor 302(9) is positioned on the back of a right hand of individual 102. Sensor 302(10) is positioned on the back of a left hand of individual 102. Sensor 302(11) is positioned on a left thigh of individual 102. Sensor 302(12) is positioned on a lower right leg of individual 102. Sensor 302(13) is positioned on a lower left leg of individual 102. Sensor 302(14) is positioned on a right foot of individual 102. Sensor 302(15) is positioned on a left foot of individual 102.

More or fewer sensors 302, in the same or different body locations, may be configured with individual 102 without departing from the scope hereof. For example, to measure finger flexibility, gloves may be configured with a plurality of sensors 302 that measure movement of each finger segment. Sensors 302 may also be configured to measure other parameters, such as temperature, heart rate, etc., without departing from the scope hereof.

In one embodiment, each sensor 302(1)-(15) measures motion (linear displacement and rotation) in three perpendicular axes X, Y and Z (often referred to as six axis measurement). Where individual 102 is to be monitored continuously (e.g., for an entire day or longer period), at least some of sensors 302 may be surgically implanted within individual 102. Certain other sensors 302 may be adhesively (e.g., as in a band aid) attached to individual 102. Certain other sensors 302 may be configured with clothing worn by individual 102. Where individual 102 is periodically but infrequently tested (e.g., certain movements tests once a week), sensors 302 may be configured with test equipment (e.g., exercise equipment). As data is collected, it is transmitted to flex server 310 that operates to create or update overall motion and/or flexibility envelope 150 of individual 102. Sensors 302 may be selected to measure one or more of displacement, velocity, and acceleration. Alternatively these parameters may be derived from other inputs (e.g., video). Regardless of the information source, motion and/or flexibility envelope 150 may take several forms—as a displacement envelope, as a velocity envelope, and as an acceleration envelope.

Figure 6:
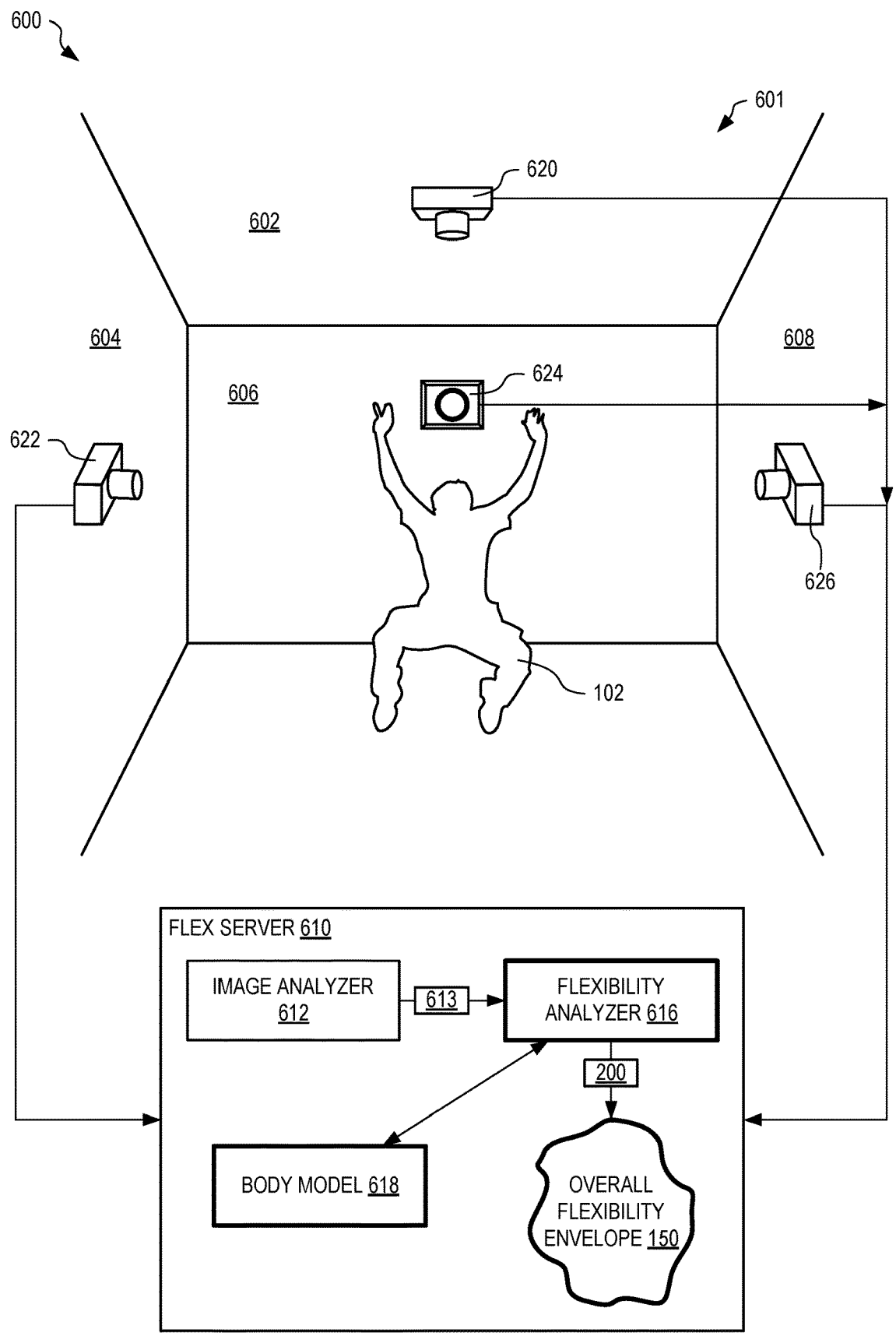
FIG. 6 shows one example system that utilizes the flex server of FIG. 3 together with a plurality of cameras mounted to capture images within a room to determine the overall motion and/or flexibility envelop of the individual, in an embodiment.

FIG. 6 shows one example system 600 that utilizes flex server 310 of FIG. 3, together with a plurality of cameras 620, 622, 624, and 626 mounted to capture images within a room 601, to determine overall motion and/or flexibility envelope 150 of individual 102. Camera 620 is configured on a ceiling 602 of room 601, and cameras 622-626 are mounted on walls 604, 606, and 608, respectively, of room 601. System 600 may have more or fewer cameras 620 without departing from the scope hereof. System 600 includes a flex server 610 that is similar to flex server 310 of FIG. 3, and includes a memory and processor that are not shown for clarity of illustration. Flex server 610 receives images (e.g., a sequence of sequentially captured images) concurrently from each camera 620, and includes an image analyzer 612 that processes these images to determine movements 613 of individual 102 within room 601. Flex server 610 also includes a motion and/or flexibility analyzer 616 and a body model 618 that are similar to flexibility analyzer 316 and body model 318 of FIG. 3. Flexibility analyzer 616 inputs movement 613 into body model 618 and determines flexibility inputs 200 for input to overall motion and/or flexibility envelope 150.

As individual 102 moves within room 601, system 600 uses cameras 620 and image analyzer 612 to process images received from each camera 620 to determine movements 613, as known in the art. In certain embodiments, visual markers are attached to certain points on the body of individual 102 to facilitate movement tracking. In another embodiment, cameras 620 capture infra-red images, wherein system 600 also includes an infrared projector (not shown) that projects a pattern into room 601 that facilitates detection of motion by individual 102.

Other methods of movement capture may be used without departing from the scope hereof. For example, exercise equipment may be configured to measure movement of individual 102 during exercise, wherein the movement information is input to flexibility analyzer 316 for conversion into flexibility inputs 200 using body model 318 and then used to form overall motion and/or flexibility envelope 150. In another example, rehabilitation equipment is configured to record movement for input to system 300.

Beyond using sensors affixed motion, gyroscope and accelerometer sensors or external cameras it should be understood that in certain embodiments other means of motion capture—e.g. heat signature from thermal cameras, or sound based signatures from audible or other sonic means or a sonar-like system or a radar-like system or a GPS type device may be utilized to ultimately generate the displacement, velocity or acceleration data for flexibility envelope 150.

Figure 7:
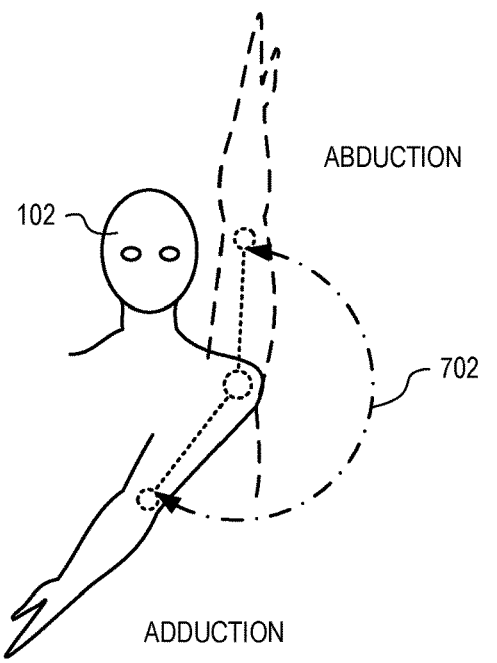
FIGS. 7, 8 and 9 show example movement of the left-shoulder of the individual.
Figure 8:
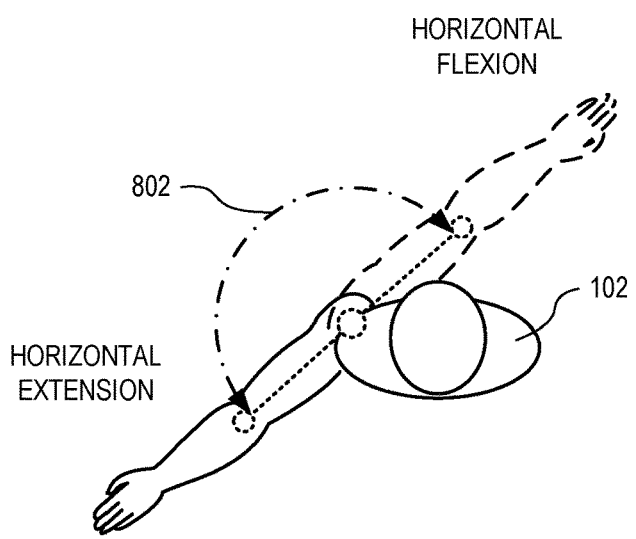
Figure 9:
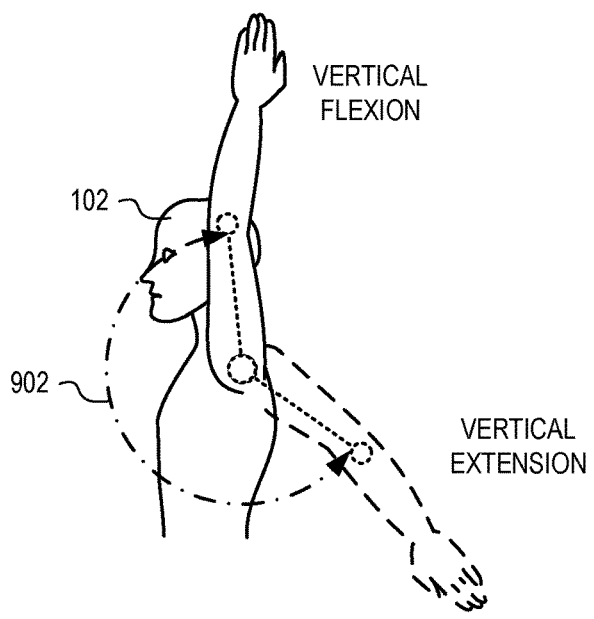

FIGS. 7, 8 and 9 show example movement of the left-shoulder of individual 102. FIG. 7 shows movement of the shoulder from abduction through adduction, giving a first range of motion 702. FIG. 8 shows the shoulder moving from horizontal flexion through a horizontal extension, giving a second range of motion 802. FIG. 9 shows the shoulder moving from vertical extension through vertical flexion, giving a third range of motion 902. FIGS. 7 through 9 thus show conventional evaluation of shoulder movement. Although each range of motion may be measured and evaluated separately, overall motion and/or flexibility envelope 150 encompasses the overall motion and/or flexibility of individual 102, and thereby allows the shoulder flexibility to be viewed as a whole as shown in FIG. 10.

Figure 10:
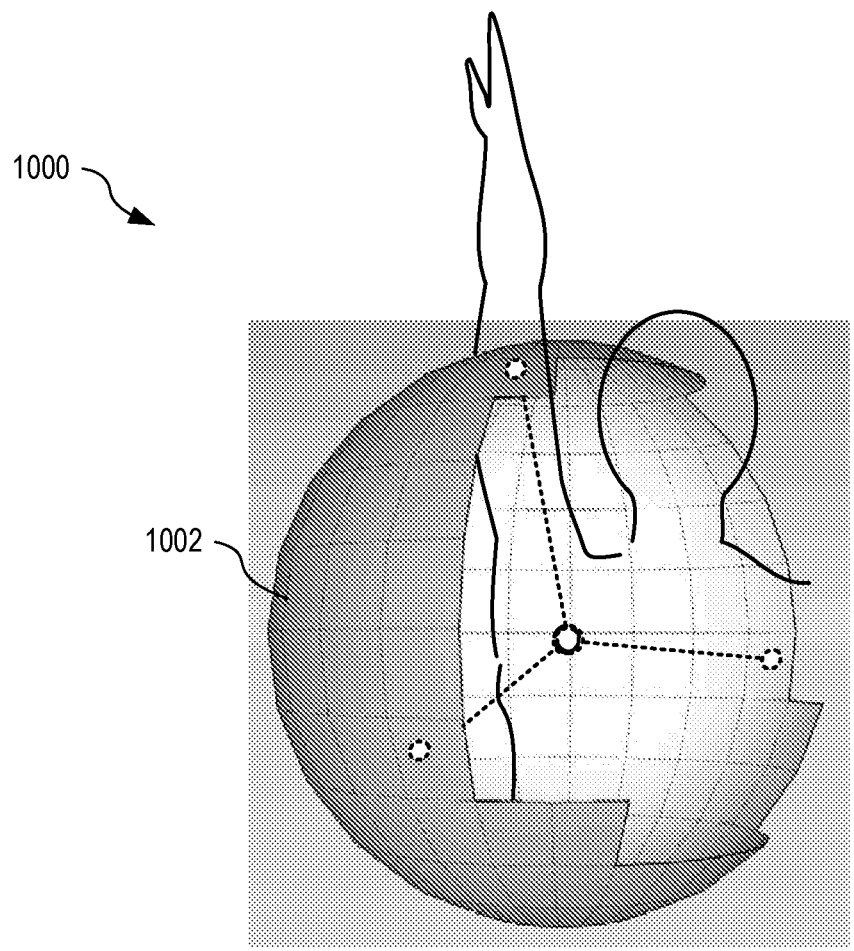
FIG. 10 shows one example rendering of shoulder motion and/or flexibility as generated from the overall motion and/or flexibility envelope of FIGS. 12, 3, and 6, in an embodiment.

FIG. 10 shows one example rendering 1000 illustrating shoulder motion and/or flexibility generated from overall motion and/or flexibility envelope 150. Rendering 1000 is from a rear perspective of individual 102, where a shell 1002 indicates overall motion and/or flexibility of the left shoulder of individual 102 by representing points where the elbow has reached relative to the torso. For example, as motion and/or flexibility inputs 200 are added to overall motion and/or flexibility envelope 150, this shell is filled based upon the achieved movement (and derived movement/flexibility) within body model 318. Overall motion and/or flexibility envelope 150 may be considered to include such shells for many, if not all, joints of individual 102, thereby allowing flexibility of one or more joints to be easily viewed and assimilated by medical practitioners and the individual.

Figure 11:
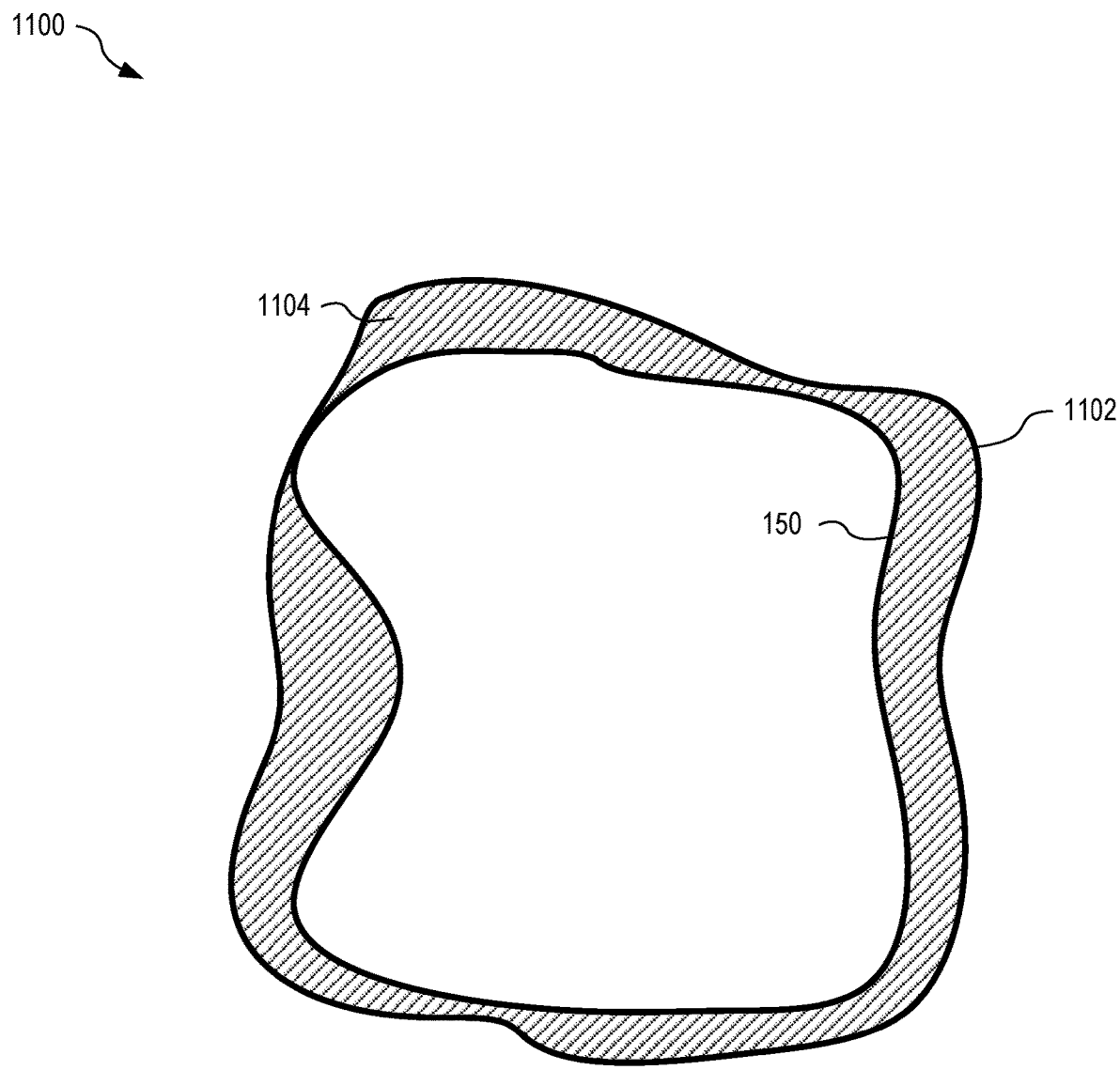
FIG. 11 shows the motion and/or flexibility envelope of FIG. 1 and an exemplary overlapping comfort/discomfort envelope, in an embodiment.

FIG. 11 shows motion and/or flexibility envelope 150 and an exemplary overlapping comfort/discomfort envelope 1102. In addition to generating motion and/or flexibility envelope 150, which is objective and quantitative, certain embodiments hereof may be configured to create overlapping comfort/discomfort envelope 1102. It is useful to understands the subjective and/or physiologic consequence of the flexibility range defined within overall motion and/or flexibility envelope 150 and the coordinate physiologic or subjective feelings of the organism, particularly when moving at extreme ranges of overall motion and/or flexibility envelope 150. Overall motion and/or flexibility envelope 150 is represented as an inside line, and an outside line represents comfort/discomfort envelope 1102. As individual 102 moves at the extremes of overall motion and/or flexibility envelope 150 using the motions of the body and/or each flex element needed to achieve this motion and/or flexibility, individual 102 may subjectively experience more discomfort as they achieve these extremes of overall motion and/or flexibility envelope 150. For example, where no discomfort occurs, comfort/discomfort envelope 1102 may have the same shape and size as overall motion and/or flexibility envelope 150. However, where discomfort occurs, comfort/discomfort envelope 1102 may extend beyond overall motion and/or flexibility envelope 150 to indicate the discomfort, as indicated in FIG. 11 by shaded area 1104. In one embodiment, inputting contemporaneous discomfort or pain information—either verbally with coordinate time synched recording, or physiologic parameters such as increasing heart rate or BP—allows greater granular component information of motion and/or flexibility envelope 150 to be revealed. For example, in a given individual while their quantitative flex/motion envelope might not change between two time points (e.g. one while well trained, another while immobile for a period of time), the quality and the subjective feeling and/or objective physiologic response (i.e. painfulness) as indicated by comfort/discomfort envelope 1102 may vary. Showing the overlap between subjective and physiologic parameter response further enriches the information obtained, and provides both objective as well as subjective information that is useful to assess, counsel, train and/or intervene in and with the organism (e.g., individual 102). System 300 may generate, analyze and display overlapping envelopes and the interaction between these envelopes may be analyzed as well.

In the embodiments described herein, the motion, flex and subjective comfort discomfort envelopes may be determined, stored, displayed and analyzed on a handheld device—e.g. smartphone tablet, smartwatch, phablet, or analogous digital or analog display and analysis means. Similarly, a desktop, laptop, mainframe or other computer system or embedded hardware, firmware system may be utilized. The embodiments described herein may also be embedded into a medical device—e.g. a holter monitor, event monitor, implanted pacemaker or defibrillator, stent, valve, sensor, pump system, orthopedic device, implant or system; metabolic, respiratory, neural, auditory, otic, ophthalmic, gastrointestinal or other physiologic system device, implant or system.

In the embodiments described herein, the data may be telemeter or otherwise sent to a secondary repository, storage or analysis system and/or up to a 'cloud." Similarly, said signals and data may be retrieved form the like.

In the embodiments described herein, data may be sent via electromagnetic, radiofrequency, telephonic, optical, thermal, electro-optical, Bluetooth, near field or other transmission means.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween. In particular, the following embodiments are specifically contemplated, as well as any combinations of such embodiments that are compatible with one another:

(A) A method for determining an overall motion and/or flexibility envelope for an individual, including capturing movement and position data of the individual, and processing the movement and position data to generate an overall motion and/or flexibility envelope for the individual defining overall motion and/or flexibility of the individual.

(B) In the method denoted as (A), the movement and position data being captured from at least two sensors configured with the individual.

(C) In either of the methods denoted as (A) and (B), the movement and position data being captured from one sensor configured with the individual over time.

(D) In any of the methods denoted as (A)-(C), the sensors being implanted within the individual.

(E) In any of the methods denoted as (A)-(D), the at least two sensors being selected from the group including strain gauges, accelerometers, gyroscopes, displacement sensors, proximity sensors, hall effect sensors, optical encoders, potentiometers, linear and rotary sensors, eddy-current sensors, reflective light sensors, pressure sensors, force sensors, tilt sensors, and vibration sensors.

(F) In any of the methods denoted as (A)-(E), the movement and position data being determined by analyzing imagery of the individual captured by one or more cameras.

(G) In any of the methods denoted as (A)-(F), the step of processing including manipulating a digital model of the individual based upon the movement and position data to determine and derive movement and flexibility of at least one joint of the individual.

(H) In any of the methods denoted as (A)-(G), the step of processing the movement and position data including comparing a currently determined overall motion and/or flexibility envelope of the individual to a previously determined overall motion and/or flexibility envelope of the individual to identify changes in flexibility of the individual.

(I) In any of the methods denoted as (A)-(H), the step of processing the movement and position data including comparing a currently determined overall motion and/or flexibility envelope of the individual to an expected overall motion and/or flexibility envelope.

(J) A system for determining an overall motion and/or flexibility envelope for an individual, including a flexibility server having memory and a processor and adapted to receive movement and position data of the individual, a motion and/or flexibility analyzer, implemented as machine readable instructions stored in the memory and executed by the digital processor, capable of processing the movement and position data to generate an overall motion and/or flexibility envelope for the individual defining overall motion and/or flexibility of the individual.

(K) The system denoted as (J), further including at least one sensor configured for sensing and generating the movement and position data.

(L) In either of the systems denoted as (J) and (K), the sensors including one or more of implantable sensors implantable in the individual to sense the movement and position data from the individual's body, wearable sensors that attach to the individual's body to sense the movement and position data, and off the body sensors for sensing the movement and position data from the individual.

(M) In any of the systems denoted as (J)-(L), the off body sensors comprising one or both of a machine for sensing the individual's movement and position, and at least two cameras for sensing the individual's movement and position.

(N) Any of the systems denoted as (J)-(M), further including an image analyzer, implemented as machine readable instructions stored in the memory and executed by the digital processor, capable of processing images from the at least two cameras to determine the movement and position data.

(O) Any of the systems denoted as (J)-(N), further including a relay device for receiving the movement and position data from the sensor and for sending the movement and position data to the flexibility analyzer.

(P) In any of the systems denoted as (J)-(O), further including an envelope display generator, implemented as machine readable instructions stored in the memory and executed by the digital processor, capable of interactively providing a view of at least part of the overall motion and/or flexibility envelope.

(Q) In any of the systems denoted as (J)-(P), the envelope display generator further capable of comparing and displaying a difference between the overall motion and/or flexibility envelope and a recorded motion and/or flexibility envelope.

(R) Any of the systems denoted as (J)-(Q), further including a body model implemented within the memory and operable to model one or more of size, weight, and movement of the individual.

(S) Any of the systems denoted as (J)-(R), further including an output device for prompting the individual to move at least part of the individual through a range of suggested or designated motions.

(T) In any of the systems denoted as (J)-(S), said motions being performed to the limit of acceptable discomfort or capability.

(U) A system for determining an overall motion envelope for an individual, including means for capturing motion of the individual, means for recording and analyzing said motion data, means for storing raw and processed information, means for converting the motion data into a flexibility envelope, means for displaying the flexibility envelope, and means for comparing the flexibility envelope at differing time points and under differing conditions.

(V) In the system denoted as (U), the motion being determined via flexibility of one or more of: the individual overall, a component of the individual, and a flex element of the individual.

(W) Either of the systems denoted as (U) and (V), further including means for capturing both objective motion and objective physiologic response to the motion.

(X) In any of the systems denoted as (U)-(W), the objective physiologic response including one or more of heart rate, blood pressure, degree of sweating, heart rate variability, blood pressure variability, catechol levels, and other markers of stress.

(Y) In any of the systems denoted as (U)-(X), the objective physiologic response allowing contemporaneous capture, analysis and generation of a comfort/discomfort/physiologic response/consequence envelope overlapping the motion/flexibility envelope.

(Z) In any of the systems denoted as (U)-(Y), the objective physiologic response allowing the determination of the consequences of these interactions.

(AA) In any of the systems denoted as (U)-(W), the contemporaneous sound or physiologic data being inputted to allow overlay and/or contemporaneous time-synched analysis of said data to determine pain or discomfort envelope or contours overlaying the motion/flex envelope.

(AB) Any of the systems denoted as (U)-(AA), further including input sensors that are applied, implanted or otherwise affixed position sensors, including accelerometers, gyroscopes strain gauges.

(AC) In any of the systems denoted as (U)-(AB), the input sensors being capable of sensing one or more of image, sound, heat, vibration, odor/vapors, and chemical markers detectors.

(AD) In any of the systems denoted as (U)-(AC), the data from the input sensors being used to determine the motion and flexibility.

(AE) In any of the systems denoted as (U)-(AD), the flexibility envelope based upon one or more of motion (dimension), velocity, and acceleration data.

(AF) Any of the systems denoted as (U)-(AE), further including means for portraying the flexibility envelope in one or more of a 2D, a 3D and a 4D representation.

(AG) In any of the systems denoted as (U)-(AF), the motion and/or flexibility envelope being captured from motion that is either active/volition or stimulated.

(AH) In any of the systems denoted as (U)-(AG), the motion and/or flexibility envelope being captured from motion that is passive and/or done by third party or device.

(AI) In any of the systems denoted as (U)-(AH), the motion and/or flexibility envelope being captured from flexibility that is the same, greater or less than the motion envelope.

(AJ) In any of the systems denoted as (U)-(W), further including capturing a comfort/discomfort envelope that is subjective.

(AK) A method for determining an overall motion and/or flexibility envelope for an individual, including capturing movement and position data from at least one sensor or motion detection means configured with the individual, analyzing the movement and position data to generate the overall motion and/or flexibility envelope for the individual, and generating a display from the overall motion and/or flexibility envelope to show motion and/or flexibility of the individual.

(AL) The method denoted as (AK), further including comparing comparative states of the flexibility envelope over time.

(AM) Either of the methods denoted as (AK) and (AL), further including prompting the individual to perform a program of motions, exercises or suggested movements to define whole body or regional motion, flexibility and subjective difficulty envelopes to provide standardization for comparison.

(AN) A software product having instructions, stored on non-transitory computer-readable media, wherein the instructions, when executed by a computer, perform steps for determining an overall motion and/or flexibility envelope for an individual, including instructions for capturing movement data, instructions for analyzing movement data, instructions for converting data into a graphical representation of movement in either 1, 2, 3 or 4D, and instructions for comparing movement of any aspect of full or partial flexibility envelope to either another point of time of the envelope of the same individual or of a database of performance.

(AO) The software product denoted as (AN), further including instructions for determining both quantitatively and graphically the comparative states of the envelope and of the delta (change).

(AP) A device for portraying, comparing and displaying the overall motion and/or flexibility envelope.

(AQ) A system to allow data to be sent to the cloud, be security encrypted and then downloaded by appropriate, security cleared user.

(AR) A series of instructions, exercises, directives to attempt to regain the motion/flexibility envelope if a decline has occurred, using any of the systems, methods and software products denoted as (A)-(AQ) to monitor progress and guide therapy.

(AS) In any of the systems, methods, and software products denoted as (A)-(AR), the systems, methods and devices being embedded into a medical device selected from the group including a holter monitor, event monitor, implanted pacemaker or defibrillator, stent, valve, sensor, pump system, orthopedic device, implant or system; metabolic, respiratory, neural, auditory, otic, ophthalmic, gastrointestinal or other physiologic system device, implant or system.

(AT) In any of the systems, methods, and software products denoted as (A)-(AR), the data being telemeter or otherwise sent to a secondary repository, storage or analysis system and/or up to a 'cloud."

(AU) In any of the systems, methods, and software products denoted as (A)-(AR), the data being received from a secondary repository, storage or analysis system and/or up to a 'cloud."

(AV) In any of the systems, methods, and software products denoted as (A)-(AR), the data being sent via electromagnetic, radiofrequency, telephonic, optical, thermal, electro-optical, Bluetooth, near field or other transmission means.

What is claimed is:

1. A method for determining an overall motion and/or flexibility envelope and a comfort/discomfort envelope for an individual, comprising the steps of:
   capturing movement, physiological, and position data of the individual, wherein the movement, physiological data, and position data is captured from at least two sensors; and
   processing the movement and position data to generate the overall motion and/or flexibility envelope for the individual;
   processing the physiological data to generate of the overall comfort/discomfort envelope overlapping with the overall motion and/or flexibility envelope.

2. The method of claim 1, wherein the movement and position data is captured from one sensor over time.

3. The method of claim 1, wherein the at least two sensors are implanted within the individual.

4. The method of claim 1, the at least two sensors for capturing movement and position data being selected from the group of sensors consisting of strain gauges, accelerometers, gyroscopes, displacement sensors, proximity sensors, hall effect sensors, optical encoders, potentiometers, linear and rotary sensors, eddy-current sensors, reflective light sensors, pressure sensors, force sensors, tilt sensors, and vibration sensors.

5. The method of claim 1, wherein at least one of the at least two sensors is a camera, and wherein capturing the movement, physiological, and position data further includes analyzing imagery of the individual captured by the camera.

6. The method of claim 1, wherein the step of processing further includes manipulating a digital model of the individual based upon the movement and position data to determine and derive movement and flexibility of at least one joint of the individual.

7. The method of claim 1, wherein the step of processing the movement and position data further includes comparing the currently determined overall motion and/or flexibility envelope of the individual to a previously determined overall motion and/or flexibility envelope of the individual to identify changes in flexibility of the individual.

8. The method of claim 1, wherein the step of processing the movement and position data further includes comparing the currently determined overall motion and/or flexibility envelope of the individual to an expected overall motion and/or flexibility envelope.

9. A system for determining an overall motion and/or flexibility envelope and a comfort/discomfort envelope for an individual, comprising:
   at least two sensors configured for sensing and generating movement, physiological, and position data;
   a flexibility server having memory and a processor and adapted to receive the movement, physiological, and position data of the individual;
   a motion and/or flexibility analyzer, implemented as machine readable instructions stored in the memory and executed by the digital processor, capable of:
   processing the movement and position data to generate the overall motion and/or flexibility envelope for the individual;
   processing the physiological data to generate the overall comfort/discomfort envelope overlapping with the overall motion and/or flexibility envelope.

10. The system of claim 9, wherein at least one of the at least two sensors comprises one or more of implantable sensors implantable in the individual to sense the movement and position data from the individual's body, at least one wearable sensor that attaches to the individual's body to sense the movement and position data, and at least one off the body sensor for sensing the movement and position data from the individual.

11. The system of claim 10, the at least one off the body sensor comprising one or both of a machine for sensing the individual's movement and position, and at least two cameras for sensing the individual's movement and position.

12. The system of claim 11, further comprising an image analyzer, implemented as machine readable instructions stored in the memory and executed by the digital processor, capable of processing images from the at least two cameras to determine the movement and position data.

13. The system of claim 9, further comprising a relay device for receiving the movement and position data from the at least two sensors and for sending the movement and position data to the flexibility analyzer.

14. The system of claim 9, further comprising an envelope display generator, implemented as machine readable instructions stored in the memory and executed by the digital processor, capable of interactively providing a view of at least part of the overall motion and/or flexibility envelope and at least part of the comfort/discomfort envelope.

15. The system of claim 14, the envelope display generator further capable of comparing and displaying a difference between the overall motion and/or flexibility envelope and a recorded motion and/or flexibility envelope.

16. The system of claim 9, further comprising a body model implemented within the memory and operable to model one or more of size, weight, and movement of the individual.

17. The system of claim 9, further comprising an output device for prompting the individual to move at least part of the individual through a range of suggested or designated motions.

18. The system of claim 17, wherein said motions are performed to a limit of acceptable discomfort or capability of the individual.

* * * * *